US00PP28290P2

(12) United States Plant Patent
Yamada

(10) Patent No.: US PP28,290 P2
(45) Date of Patent: Aug. 15, 2017

(54) ***PETUNIA* PLANT NAMED 'SUNMOMOHEART'**

(50) Latin Name: *Petunia×hybrida*
Varietal Denomination: SUNMOMOHEART

(71) Applicant: Masahiro Yamada, Shiga (JP)

(72) Inventor: Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 14/999,204

(22) Filed: Apr. 11, 2016

(51) Int. Cl.
*A01H 5/02* (2006.01)

(52) U.S. Cl.
USPC ..... Plt./356.13

(58) Field of Classification Search
USPC ..... Plt./356.13
See application file for complete search history.

*Primary Examiner* — Annette Para
(74) *Attorney, Agent, or Firm* — C. A. Whealy

(57) ABSTRACT

A new and distinct cultivar of *Petunia* plant named 'Sunmomoheart', characterized by its upright and mounding plant habit; vigorous growth habit; freely branching habit; freely flowering habit; long flowering period; flowers that are white in color with pink-colored heart-shaped pattern; and good garden performance.

1 Drawing Sheet

Botanical designation: *Petunia×hybrida.*
Cultivar denomination: 'SUNMOMOHEART'.

BACKGROUND OF THE INVENTION

The present invention relates to a new and distinct cultivar of *Petunia* plant, botanically known as *Petunia×hybrida* and hereinafter referred to by the name 'Sunmomoheart'.

The new *Petunia* plant is a product of a planned breeding program conducted by the Inventor in Higashiomi, Shiga, Japan. The objective of the breeding program is to create new vigorous and mounding *Petunia* plants with numerous unique and attractive flowers.

The new *Petunia* plant originated from a cross-pollination made by the Inventor in September, 2012 in Higashiomi, Shiga, Japan of a proprietary selection of *Petunia×hybrida* identified as code designation PY-293-1, not patented, as the female, or seed, parent with a proprietary selection of *Petunia×hybrida* identified as code designation PY-293-2, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in October, 2013.

Asexual reproduction of the new *Petunia* plant by vegetative terminal cuttings in a controlled greenhouse environment in Higashiomi, Shiga, Japan since November, 2013 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunmomoheart'. These characteristics in combination distinguish 'Sunmomoheart' as a new and distinct *Petunia* plant:

1. Upright and mounding plant habit.
2. Vigorous growth habit.
3. Freely branching habit.
4. Freely flowering habit.
5. Long flowering period.
6. Flowers that are white in color with pink-colored heart-shaped pattern.
7. Good garden performance.

Plants of the new *Petunia* can be compared to plants of the parent selections. Plants of the new *Petunia* differ primarily from plants of the parent selections in flower color pattern as plants of the parent selections have flowers with a star-shaped pattern. In addition, plants of the male parent selection have white and lighter pink-colored flowers than plants of the new *Petunia.*

Plants of the new *Petunia* can also be compared to plants of the *Petunia×hybrida* 'Daiichi-MP22-253-2', disclosed in U.S. Plant patent application Ser. No. 13/998,606. In side-by-side comparisons, plants of the new *Petunia* and 'Daiichi-MP22-253-2' differ primarily in the following characteristics:

1. Plants of the new *Petunia* are more mounding than and not as creeping as plants of 'Daiichi-MP22-253-2'.
2. Plants of the new *Petunia* have shorter leaves with shorter petioles than plants of 'Daiichi-MP22-253-2'.
3. Plants of the new *Petunia* and 'Daiichi-MP22-253-2' differ in flower color pattern as plants of 'Daiichi-MP22-253-2' have flowers with a star-shaped pattern.
4. Plants of the new *Petunia* have smaller sepals than plants of 'Daiichi-MP22-253-2'.
5. Plants of the new *Petunia* had shorter peduncles than plants of 'Daiichi-MP22-253-2'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet is a side perspective view of a typical flowering plant of 'Sunmomoheart' grown in a container.

The photograph at the bottom of the sheet is a close-up view of a typical flowering plant of 'Sunmomoheart'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were six months old when the photographs and description were taken. In the following description, color references are made to The Royal Horticultural Society Colour Chart, 2007 Edition, except where general terms of ordinary dictionary significance are used.

Botanical classification: *Petunia×hybrida* 'Sunmomoheart'.

Parentage:

- *Female, or seed, parent*.—Proprietary selection of *Petunia×hybrida* identified as code designation PY-293-1, not patented.
- *Male, or pollen, parent*.—Proprietary selection of *Petunia×hybrida* identified as code designation PY-293-2, not patented.

Propagation:

- *Type*.—By vegetative terminal cuttings.
- *Time to initiate roots, summer and winter*.—About one week at temperatures about 15° C. to 20° C.
- *Time to produce a rooted young plant, summer and winter*.—About three weeks at temperatures about 15° C. to 20° C.
- *Root description*.—Fibrous; typically white in color, actual color of the roots is dependent on substrate composition, water quality, fertilizer type and formulation, substrate temperature and physiological age of roots.
- *Rooting habit*.—Freely branching.

Plant description:

- *Plant form and growth habit*.—Upright and mounding plant habit; freely branching habit with numerous lateral branches developing per plant; pinching enhances lateral branch development; vigorous growth habit.
- *Plant height*.—About 20 cm.
- *Plant diameter*.—About 55 cm.

Lateral branch description:

- *Length*.—About 30 cm.
- *Diameter*.—About 1.5 mm.
- *Internode length*.—About 2.1 cm.
- *Strength*.—Strong, flexible.
- *Aspect*.—Mostly outwardly.
- *Texture*.—Densely pubescent; viscid.
- *Color*.—Close to 144A.

Leaf description:

- *Arrangement*.—Alternate, simple.
- *Length*.—About 3.8 cm.
- *Width*.—About 2.65 cm.
- *Shape*.—Elliptic.
- *Apex*.—Broadly acute.
- *Base*.—Attenuate.
- *Margin*.—Entire.
- *Texture, upper and lower surfaces*.—Pubescent; viscid.
- *Venation pattern*.—Pinnate; reticulate.
- *Color*.—Developing and fully expanded leaves, upper surface: Close to 138A; venation, close to 144B. Developing and fully expanded leaves, lower surface: Close to 138B; venation, close to 144A.
- *Petioles*.—Length: About 2.8 mm. Diameter: About 1.7 mm. Texture, upper and lower surfaces: Pubescent; viscid. Color, upper and lower surfaces: Close to 138B.

Flower description:

- *Flower arrangement and habit*.—Single-type salver-form flowers arising from upper leaf axils; freely flowering habit with usually about 131 flowers developing per plant during the flowering season; flowers face mostly upright to outwardly.
- *Fragrance*.—None detected.
- *Natural flowering season*.—Plants of the new *Petunia* initiate and develop flowers about seven weeks after planting; long flowering period, flowering commences naturally during the spring and plants flower continuously throughout the summer until late autumn in Japan.
- *Flower longevity*.—Individual flowers last about seven to ten days on the plant; flowers not persistent.
- *Flower buds*.—Length: About 3.3 cm. Diameter: About 9 mm. Shape: Cylindrical. Color: Close to 145C; towards the apex, close to 68D.
- *Flower diameter*.—About 4.4 cm.
- *Flower length (depth)*.—About 3.65 cm.
- *Flower tube length*.—About 2.25 cm.
- *Flower tube diameter, proximally*.—About 2.2 mm.
- *Flower tube diameter, distally*.—About 8 mm.
- *Corolla*.—Quantity and arrangement: Five in a single whorl, fused at the base and opening into a flared trumpet. Petal length from throat: About 1.6 cm. Petal width: About 1.7 cm. Petal shape: Roughly spatulate. Petal apex: Mucronate to truncate. Petal margin: Entire; slightly undulate. Petal texture and luster, upper and lower surfaces: Smooth, glabrous; matte. Throat texture: Pubescent. Tube texture: Pubescent. Color: Petal, when opening, upper surface: Close to NN155B; heart-shaped pattern, close to 68D. Petal, when opening, lower surface: Close to NN155B; heart-shaped pattern, close to 56A. Petal, fully opened, upper surface: Close to NN155B; heart-shaped pattern, close to 63C; venation, close to N144D; color does not change with development. Petal, fully opened, lower surface: Close to NN155D; heart-shaped pattern, close to 62B. Throat: Proximally, close to 145D; distally, close to 150D; venation, close to 145B. Tube: Proximally, close to 145D; distally, close to NN155B to NN155C.
- *Calyx*.—Arrangement: One star-shaped calyx tube with five sepals in a single whorl and fused at the base. Sepal length: About 9.5 mm. Sepal width: About 1.7 mm. Sepal shape: Lanceolate. Sepal apex: Obtuse. Sepal margin: Entire. Sepal texture, upper and lower surfaces: Pubescent; viscid. Color, upper surface: Close to 137C. Color, lower surface: Close to 137B.

*Peduncles*.—Length: About 1 cm. Diameter: About 1.1 mm. Strength: Strong, flexible. Aspect: Upright to outwardly. Texture: Pubescent; viscid. Color: Close to 144A.

*Reproductive organs*.—Stamens: Quantity per flower: Five. Filament length: About 1.5 cm. Filament color: Close to 157D. Anther shape: Ellipsoidal. Anther size: About 1.7 mm by 2 mm. Anther color: Close to 4D. Pollen amount: Moderate. Pollen color: Close to NN155C. Pistils: Quantity per flower: One. Pistil length: About 2 cm. Style color: Close to 144D. Stigma shape: Transversely ellipsoidal. Stigma color: Close to 144B. Ovary color: Close to 144B.

Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunmomoheart' as illustrated and described.

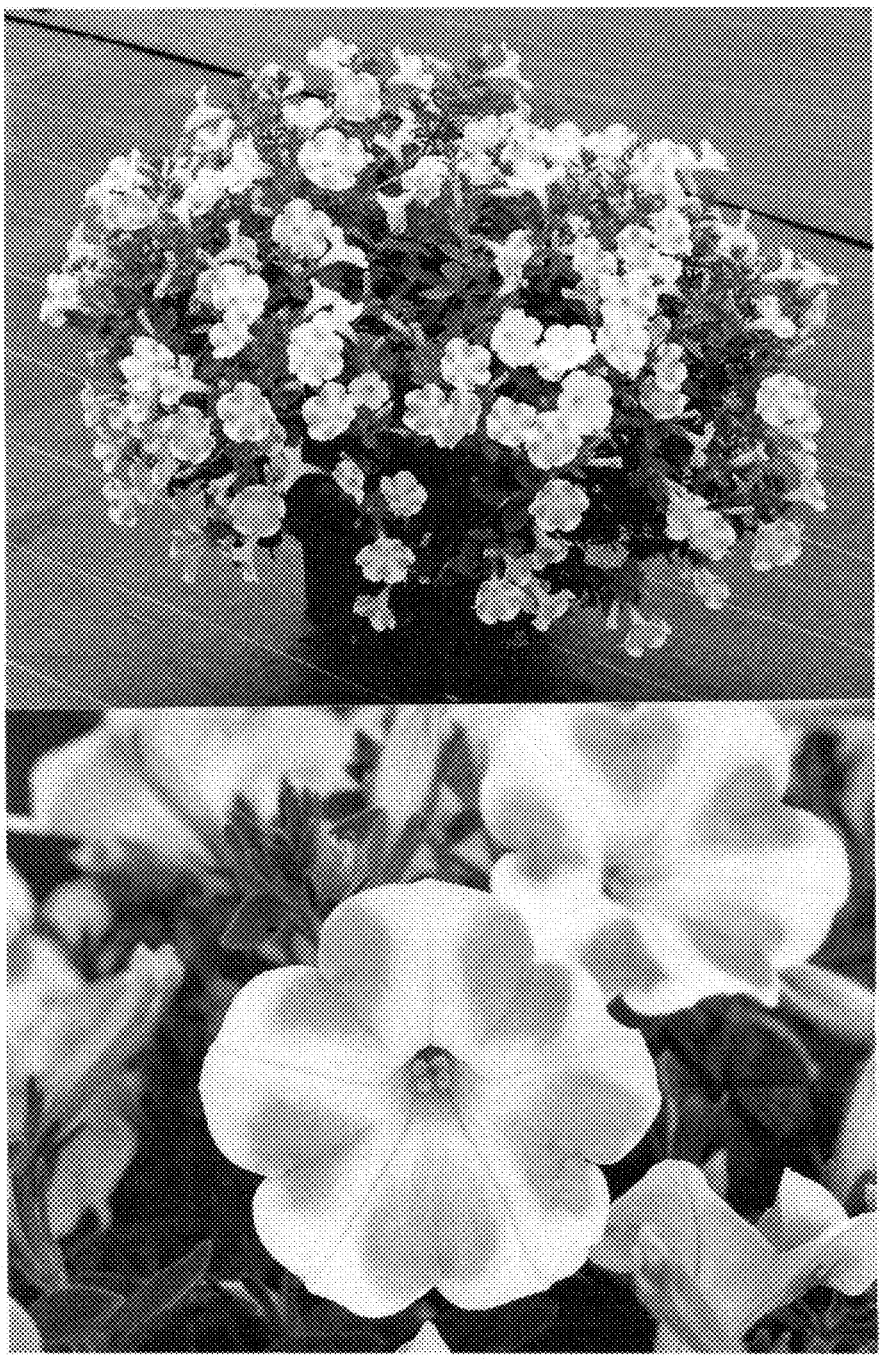

* * * * *